United States Patent [19]

Gupta

[11] Patent Number: 5,648,996
[45] Date of Patent: Jul. 15, 1997

[54] TANGENTIAL COMPUTERIZED TOMOGRAPHY SCANNER

[75] Inventor: Nand K. Gupta, Libertyville, Ill.

[73] Assignee: Omega International Technology, Inc., Lakemoor, Ill.

[21] Appl. No.: 511,111

[22] Filed: Aug. 4, 1995

[51] Int. Cl.⁶ .................................................. G21K 5/10
[52] U.S. Cl. ................... 378/4; 378/11; 378/146
[58] Field of Search .................. 378/146, 4, 11, 378/55, 57, 58, 193, 196, 189, 190, 62, 195, 208

[56] References Cited

U.S. PATENT DOCUMENTS

| | | |
|---|---|---|
| 3,766,387 | 10/1973 | Heffan et al. . |
| 3,937,965 | 2/1976 | Vasseur . |
| 4,029,963 | 6/1977 | Alvarez et al. . |
| 4,160,165 | 7/1979 | McCombs et al. . |
| 4,160,167 | 7/1979 | Weiss et al. . |
| 4,543,490 | 9/1985 | Gupta . |
| 4,709,382 | 11/1987 | Sones . |
| 4,833,698 | 5/1989 | Flannery et al. . |
| 4,845,731 | 7/1989 | Vidmar et al. . |
| 4,852,131 | 7/1989 | Armistead ................................ 378/58 |
| 4,975,934 | 12/1990 | Sauerwein et al. . |
| 4,989,225 | 1/1991 | Gupta et al. . |
| 5,012,498 | 4/1991 | Cuzin et al. . |
| 5,023,895 | 6/1991 | McCroskey et al. . |
| 5,119,408 | 6/1992 | Little et al. . |
| 5,138,642 | 8/1992 | McCroskey et al. . |
| 5,359,639 | 10/1994 | Saito ....................................... 378/146 |
| 5,432,834 | 7/1995 | Gershman .............................. 378/146 |

OTHER PUBLICATIONS

Research and Development Contract (No. N60921-93-C-A304), Nand K. Gupta and G.R. Vaughan (Naval Surface Warfare Center), dated Nov. 27, 1992.

*Primary Examiner*—Don Wong
*Attorney, Agent, or Firm*—Brinks Hofer Gilson & Lione

[57] ABSTRACT

A tangential computer tomography scanner for scanning an object having a cross-section. A radiation source emits a beam of penetrating energy. The beam penetrates an object located within the beam and is received by an array of detectors located opposite the source. A drive device moves the beam relative to said object. The array and the source are arranged so that the beam is maintained perpendicular to the cross-section of the object. The tangential computer tomography scanner generates a full volume data set in a single pass.

31 Claims, 6 Drawing Sheets

TANGENTIAL COMPUTERIZED TOMOGRAPHY SCANNER

The invention described herein was made with Government support under contract No. N60921-93-C-A304 awarded by the Naval Surface Warfare Center. The Government has certain rights in the invention.

BACKGROUND OF THE INVENTION

Computerized tomography ("CT") scanning systems were initially developed to provide a non-invasive means for viewing internal organs and tissues of the human body. CT scanners have also been developed for industrial applications to allow for non-destructive testing. For example, a CT scanner may be used for viewing cross-sections of structurally critical parts, such as rocket motors or barrels of nuclear or toxic waste. A small imperfection or void in a rocket motor casing can lead to fracturing or cracking during the firing process due to the resultant high stresses imposed on the rocket casing. Voids or unbond defects formed between the liner of a rocket motor and solid propellant contained therein can also create problems when the rocket is fired.

For example, when a rocket motor contains voids or unbond defects, it can fire in an unintended manner. This can lead to error in the velocity of the payload and, more importantly, to error in the direction of travel of the payload. Although guidance systems, using gyroscopes, can correct for small errors, those systems are often incapable of correcting large errors. As a result, the payload can arrive at the wrong location at the wrong time.

Nuclear and toxic waste present yet another industrial dilemma as the waste can corrode and weaken storage containers. Therefore, barrels containing such waste need to be analyzed periodically to ensure that the integrity of the barrel wall remains intact. Failure can create extremely hazardous situations.

As small flaws in any of these applications can lead to disastrous results, an inspection system needs to be both sensitive and accurate. However, pursuant to normal economic constraints and the higher rates of production associated with industrial applications, industrial scanners need to be relatively fast and yet inexpensive.

Typical CT scanning involves directing a source of radiation at a detector while simultaneously interposing the object to be scanned between the radiation source and the detector. The radiation source emits a beam of radiation that penetrates and passes through the object. Depending on the density, size and composition of the object, the beam is attenuated to varying degrees as it passes through the object. The resultant levels of radiation intensity are received by the detector and recorded by a computer. This basic concept has been modified and adapted over a period of time resulting generally in four generations of medical and industrial CT scanners.

The first generation of CT scanner uses only one x-ray detector. A pencil x-ray beam is formed between an x-ray source and the single detector. The pencil beam is traversed through the object or patient to be scanned. The detector receives and measures the variant intensity of the pencil beam and transmits the measured values to a computer that collects and analyzes the data. The pencil beam is then translated a small increment along the length of the object and makes another parallel pass through the cross-section of the object.

For complete image reconstruction of the object being scanned, a multiplicity of parallel passes must be made by the beam. After the desired number of parallel cross-sectional passes are made, the pencil beam is rotated by a small angle, typically one degree, and the entire translational measurement process is repeated. Complete image reconstruction, therefore, involves repeating the translational process until a complete 180 degree scan is completed. For example, the translational process is repeated 180 times for a one degree angle of rotation. With this arrangement, a lot of time is spent in starting and stopping the machine between each traverse and each rotation. With a first generation scanner, therefore, the time for scanning an object is extremely long and is prohibitive for almost all industrial applications.

Although scanning time severely limits the applications of the first generation scanner, it has some advantages. Because only one detector is utilized, the reconstructed image produced by this system does not have any aberrations or artifacts. In systems that use more than one detector, data is collected by different detectors which may receive and report slightly different values for the same intensity of radiation. When the data is reconstructed into an interior image by combining the data from different detectors, artifacts may appear which reflect nothing more than detector variance. Thus, cross-sectional images reconstructed from a scanner using only one detector are devoid of all artifacts and the resulting reconstructed image is of high quality.

A second generation scanner uses a fan shaped x-ray beam of about 30-60 degrees and a plurality of detectors arranged along a line. The plane formed by the beam lies parallel to the cross-section being analyzed. The fan beam is passed through the object and is received by the detector array. In scanning an object, the leading edge of the fan beam, defined by the signal received by the first detector, must begin its scan at the outside edge of the object and the trailing edge of the fan-beam, or signal received by the last detector, must exit the object. Therefore, extraneous data is collected at the beginning and end of each pass as the majority of detectors receive signals completely outside the object. Collection of extraneous data consumes data space and computer time and needlessly increases scanning times.

When activated, a second generation fan-beam makes one cut across the object. The object is then rotated relative to the beam by the angle of the fan-beam and another cut is made and the data recorded. For example, a typical 30 degree fan beam requires 5 rotations to complete a 180 degree scan. When compared to a first generation scanner, the overall scan time is greatly reduced. However, as with first generation scanners, a great deal of time is consumed in starting and stopping the scanner between each traverse, and in collecting extraneous data.

Although quicker, second generation scanners can produce some artifacts in the reconstructed images. Since multiple detectors are used, there are variations between the responses recorded by the detectors. These variations produce small mismatches at different angles of the entire data set. When reconstructed, therefore, the image can contain artifacts. Although computer software can remedy this problem by making corrections for detector variations, the artifacts are never completely eliminated.

Third generation CT scanner systems use an x-ray source which directs a fan-shaped beam of radiation at a planar array of detectors usually, but not always, arranged in an arc. The cross-section of the object to be scanned fits within the fan-shaped beam so that the entire cross-section is covered by the beam. The x-ray source and detector array are then rotated relative to the object until a data set is collected. For a subsequent CT slice, the object is traversed along its length and another set of data is generated. This type of scanner eliminates translation of the x-ray beam or object during the data collection for a single CT slice. In essence, the x-ray source and detector array only rotate during the collection of data for one CT slice. The total scanning time is therefore greatly reduced as no traverse is required.

However, third generation systems also have some limitations. For instance, the size of the object to be scanned is limited by the size of the beam, as the object must fit within it. If large objects are to be scanned, a greater number of detectors is required and the cost can become prohibitive. Conversely, if the object is smaller than the fan beam, extraneous data is collected by detectors receiving radiation signals passing outside the object. Unused data occupies data space and extends computation and scanning times.

In third generation systems, the detector variations can create very significant artifacts in the reconstructed images. Many times, third generation systems are not used in industrial applications due to the pronounced circular artifacts. In addition, the total number of rays collected is limited by the number of detectors in the detector array. In some cases, this can limit the spatial resolution of the system. To obtain better image resolution of the reconstructed image, one must add more detectors to the array. This procedure can be costly.

A fourth generation system consists of an array of detectors positioned in a circle. A large number of detectors is needed to obtain reasonably good resolution and the system can be very expensive. The object is positioned within the circle and a radiation source emits radiation that penetrates the object and is received by the detector array. Only objects fitting within the x-ray fan beam can be scanned with this type of system. Conversely, if a small object is scanned, the detectors collect extraneous data from the radiation beams falling outside the object. The total number of views collected during the data collection is limited by the number of detectors in the detector array. In some cases, this can limit the spatial resolution of the system. To obtain better image resolution of the reconstructed image, one must add more detectors to the array. This procedure can be very costly.

As disclosed in U.S. Pat. No. 4,989,225, CT scanners have also been developed which simultaneously rotate and translate an object during a scan. This process makes it unnecessary to perform sequential passes or to relocate the source and detectors between passes to complete a scab. However, although throughput is greatly increased, multiple detectors are still utilized to image a cross-section and the reconstructed image contains artifacts. Furthermore, this process must be repeated for different cross-sectional slices because the data is collected for one slice at a time. To collect the data for the entire volume of the object, one must collect data for many individual slices.

In conclusion, all of the previous generations of CT scanners have one or more of the following disadvantages: prohibitive scanning time, object cross-section size limitations, artifacts in cross-sectional images, extraneous data collection, or detector dependent image resolution.

It is an object of this invention, therefore, to provide a CT scanner capable of single-pass, full-volume scanning. It is also an object of this invention to provide a CT scanner capable of accommodating various cross-sectional size objects without corresponding detector array variations or extraneous data collection. Yet another object of this invention is to provide variable image resolution not dependent on the detector array configuration. Finally, it is an object of this invention to eliminate or reduce reconstructed cross-sectional image artifacts.

SUMMARY OF THE INVENTION

Briefly stated, the present invention is directed to a CT scanner system for the tangential scanning of an object by a beam of penetrating energy emitted by an energy source and received by a detector array. The detector array and the energy source are positioned such that the beam is perpendicular to a cross-section of the object. The object is moved relative to the beam of penetrating energy. Each detector measures the intensity of the beam as it passes through the object. Each detector generates data for its own unique cross-section which is stored by a computer for eventual reconstruction and display. As the entire length of the object is being scanned during a single pass, only one pass is required to generate data for reconstruction of the entire volume of the object.

For a complete volume scan, the scan begins with the beam located at the edge of the object, thereby forming a tangent to the object. The object is rotated and simultaneously translated through the beam. The beam generates data along tangential paths of varying diameter circles, each detector generating data for its own unique cross-section or slice. 180 degree data sets are generated by passing the beam through the object from the object's outer diameter to the object's center. 360 degree data sets are generated by passing the beam through the entire diameter of the object as it rotates. With both the 180 and 360 degree scans, no data is collected outside the object, regardless of the objects size. Therefore, the scanning time is reduced because the starting and stopping points of the scan are adjusted to accommodate the diameter of the object being scanned.

If more data is required for better resolution in the reconstructed image, the rotation and translation speeds can be altered to allow for the generation of more views and data points. Image resolution, therefore, can be immediately improved without having to install more detectors. Conversely, if quick scan times are of paramount importance, and coarser images are sufficient for the analysis at hand, the scanning process can be altered to immediately accommodate these parameters by increasing rotation and/or translation speeds.

In one aspect of the invention, the data generated from a single pass of a tangential CT scanner is arranged in a data cube for display in one of three modes. First, a tangent display retrieves the data for each layer of data generated at the tangential layer of the object. This is analogous to unraveling a roll of paper, the roll of paper representing the object. Each sheet represents a tangential layer of data.

A second display is the sinogram display where the data is retrieved to display a sinogram for each cross-section. This is a vertical slice through the data cube and the data in that slice is generated by individual detector. Because a single detector gathers data for each cross-section, reconstructed images using this data have no artifacts.

A third type of display is the radiograph display, where the data is retrieved to display a digital radiograph of the object. This data is a horizontal slice through the data cube and this entire slice is generated for the object at a fixed azimuthal location. Successive layers in this mode are radiographs after a slight rotation of the object.

DETAILED DESCRIPTION OF THE INVENTION

Figure 1:
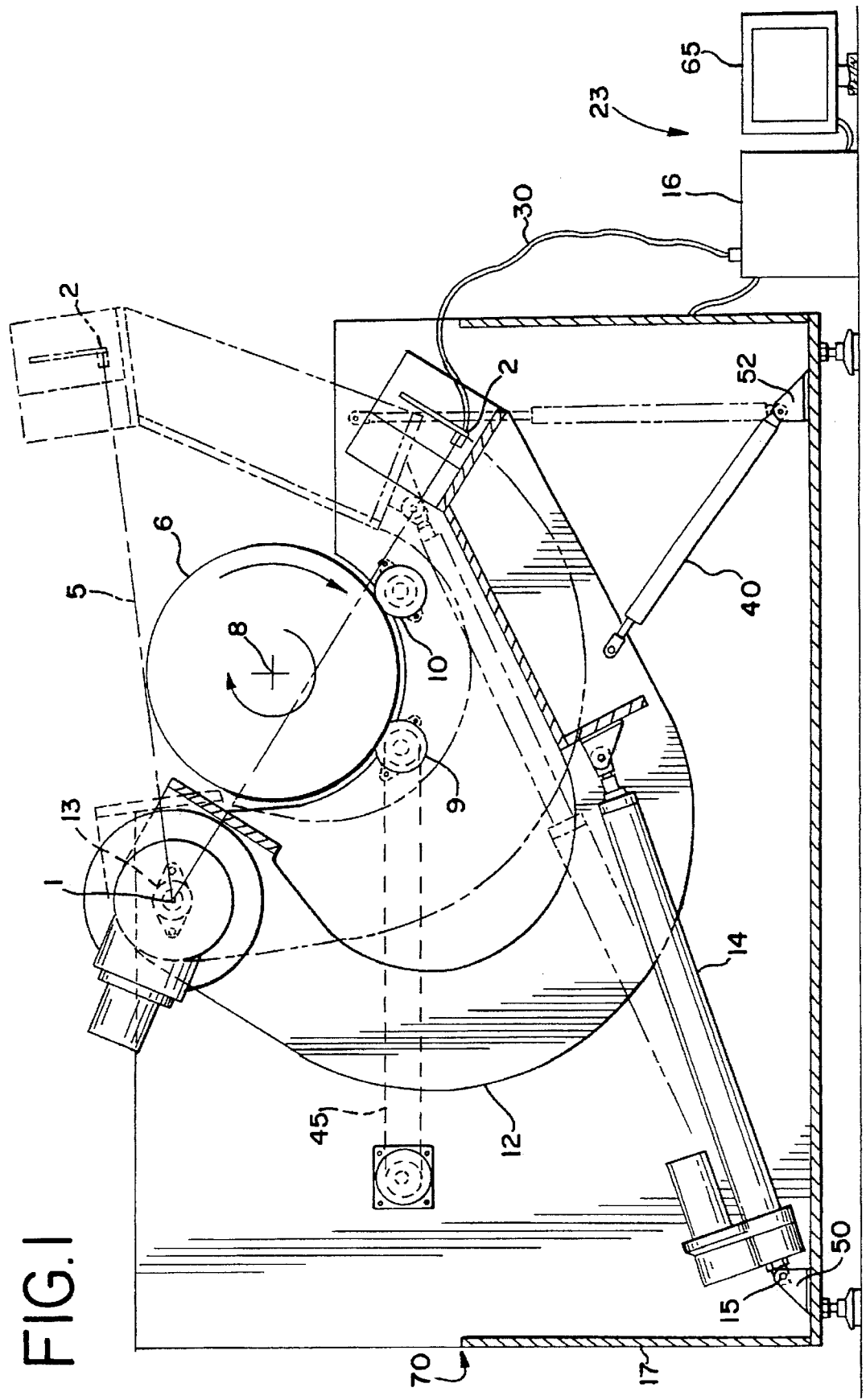
FIG. 1 is a side view of a preferred embodiment of a tangential CT scanner having an arcuate path about an object.
Figure 2:
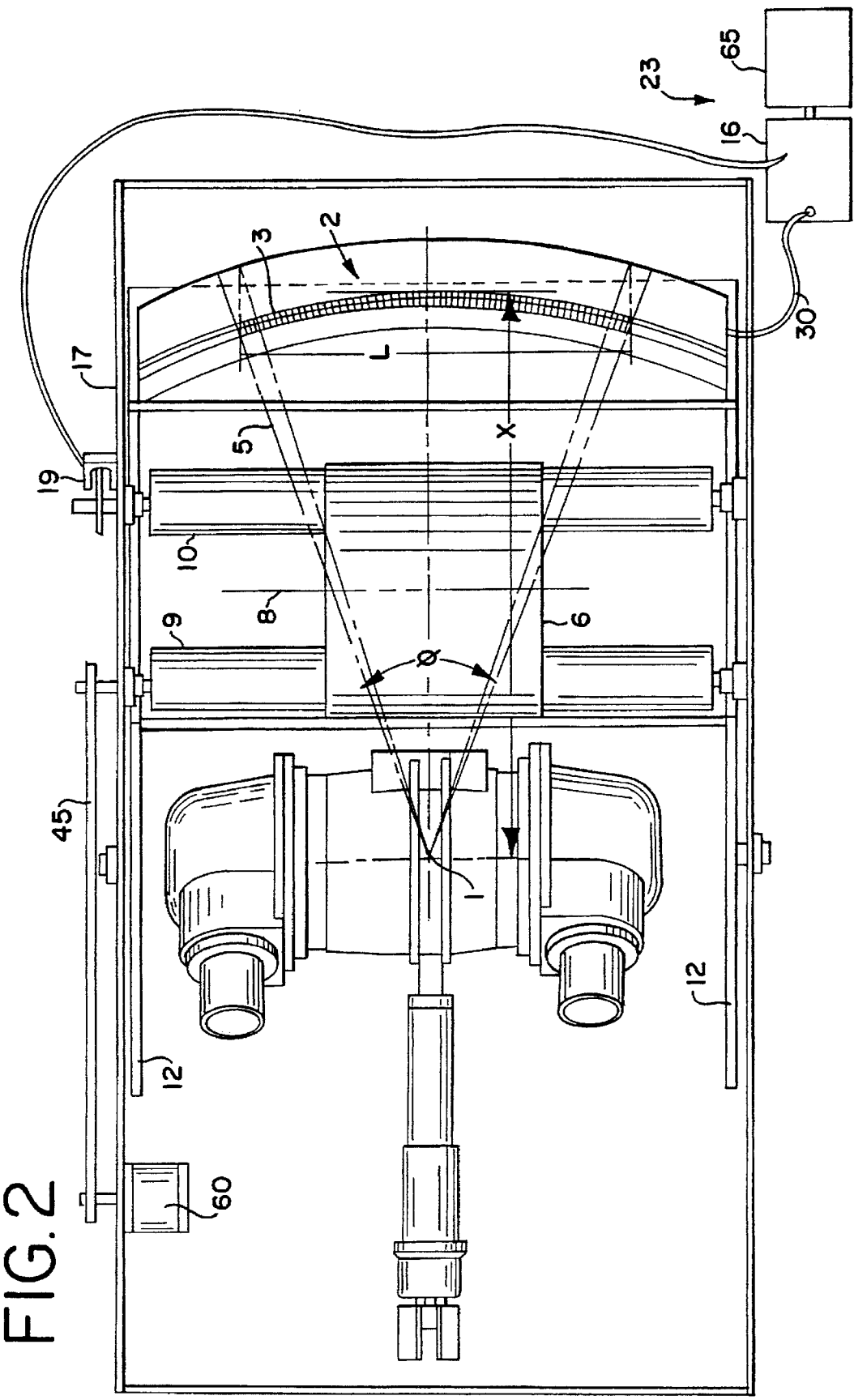
FIG. 2 is a top view of a tangential CT scanner of FIG. 1 having an arcuate path about an object.

FIG. 1 shows a preferred embodiment of a tangential CT scanner system in accordance with the present invention. The system has a penetrating energy source 1. For example, a suitable x-ray source is in the 300 kV to 450 kV output range such as the Pantak 320 kV high frequency constant potential x-ray tube. As shown in FIG. 2, the system includes a plurality of detectors 3, generally x-ray detectors, positioned in a linear or arcuate arrangement that functions as a detector array 2. As depicted, the detector array 2 shown has about 160 solid state x-ray detectors. When activated, the penetrating energy source 1 emits radiated energy that passes through an object 6 to be scanned, depicted in FIGS. 1, 2 and 5 as a simple cylinder. The radiated energy is received by the detector array 2, forming a planar fan-shaped beam of penetrating energy or fan-beam 5. The detectors 3 measure the intensity of the fan-beam 5 as received. The fan-beam 5 is attenuated as it passes through various features of the object 6. The varying intensities of radiation are registered by the detectors 3 and define the features of the object 6 as it is scanned.

The tangential CT scanner is ideally suited for analysis of circular type objects 6, such as rocket motors or barrels of toxic or nuclear waste. It should be understood that a multiplicity of objects such as pistons and turbines can also be analyzed with the tangential CT scanner. In addition, other types of noncylindrical objects can also be scanned.

With respect to rocket motors, manufacturers need to analyze the rocket fuel and other sections of the interior of the motor, without destroying the motor. Analysis of the rocket motor fuel for unbond defects, voids and inclusions is critical as any defect or impurity can cause failure of the rocket motor or result in the payload arriving at the wrong destination. For example, unbond defects are a problem because they are very difficult to detect, as they are very narrow and lie along the inner surface of the rocket motor. Indeed, normal radiographic methods cannot detect them. Accordingly, it is common in the industry to use tangential film radiographic methods to detect such defects. Using this method, an object is interposed between a film and an x-ray source, which penetrates the object. When the film and x-ray are parallel to the defect, it appears in the film. Because only a limited number of tangential film radiographs can be taken, however, unbond defects can be missed. Failures initiated by such defects can be catastrophic.

Figure 3:
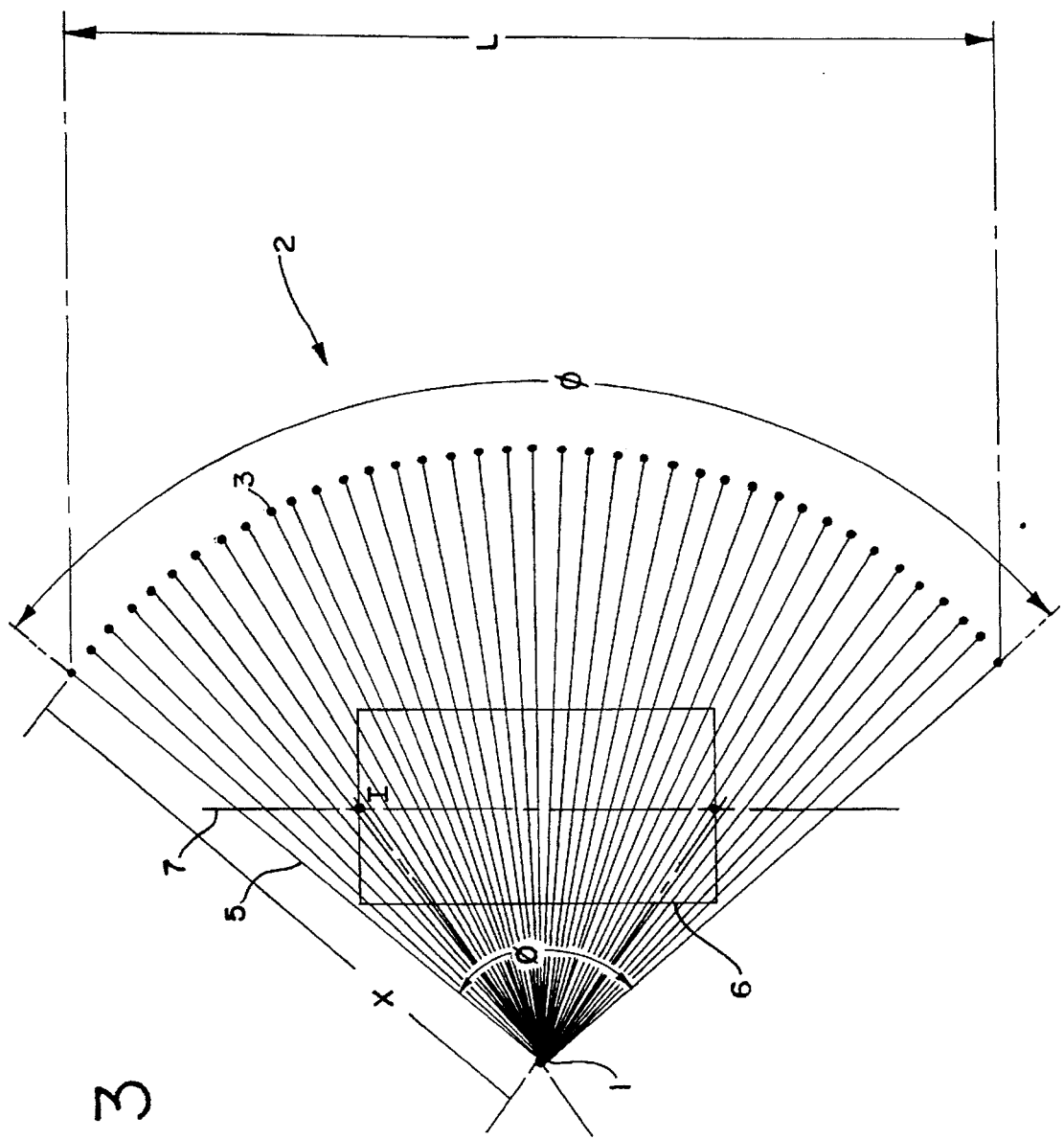
FIG. 3 is a top view of a tangential radiation fan beam passing through an object and received by a detector array.

For a simultaneous CT scan of the entire volume of the object 6, the entire object 6 must fit within the beam 5, as shown in FIG. 3. When the entire object 6 fits within the x-ray beam 5, the tangential CT scanner system simultaneously collects CT cross-sectional data for all slices. In essence, the height or length of the object 6 must lie within the beam 5 of penetrating energy for simultaneous scanning of the entire volume of the object 6 as shown in FIG. 3.

The fan-beam 5 is defined by the length of the array 2 (L) and the angle φ. Therefore, the size of the object 6 to be scanned dictates both the length of the array (L) 2, which can be varied by increasing or decreasing the distance between each detector 3, and the distance (X) between the array 2 and the energy source 1. These parameters, in turn, control the size of the angle φ. In an exemplary embodiment, 160 detectors 3 are used in the detector array 2 and can accommodate a ten inch long rocket motor. The number of detectors 3 and the space between them does not dictate, however, the level of geometrical resolution of the displayed image. Rather, resolution is a function of rotation and translation speeds. The number of detectors 3 only determines the number of cross-sectional CT slices.

Several types of scanning are available. For example, the object 6 can be translated relative to the energy beam 5 without concurrent rotation. This type of scan generates a radiographic image of the object 6. Conversely, the object 6 can be rotated relative to the energy beam 5 without concurrent translation. This type of scan provides a single tangential layer of the object 6. Finally, to obtain full volume data, the object 6 is simultaneously rotated and translated relative to the energy beam 5.

When the scanner is activated to collect full volume data, a drive device 70 rapidly rotates the object 6 to be scanned about an axis 8 parallel to the orientation of the detector array 2. Typically, the objects 6 to be scanned are cylindrical in nature, such as rocket motors or drums holding nuclear or toxic waste. The speed of rotation can be varied, depending on the degree of resolution required, but is generally about 10–100 rpm.

In a gantry embodiment, used for scanning circular objects 6 as shown in FIGS. 1 and 2, the object 6 is rotated about its own cylindrical axis 8, or axis of symmetry, and is supported by two rollers 9 and 10; a drive roller 9 that induces rotation, and a recorder roller 10 that has an encoder 19, such as the Dynapar encoder, Model No. M2005001003107. In an exemplary embodiment, the drive roller 9 is connected to a servo-motor 60 with a timing belt 45. The encoder 19 tracks the azimuthal location of the object 6 as it rotates. As data points are recorded, the position of the object 6 is recorded and transmitted to a computer 23.

The azimuthal location of the object 6 provides the exact path of the x-ray beam 5 through the object 6 at any given time. This information is used in analyzing the data. For example, it can provide the exact location of any flaw or defect found by the tangential scanning system. When the data from the tangential CT scanner is used for reconstructing cross-sectional CT images, the azimuthal location information is used, during the back projection, for proper image reconstruction.

Figure 6:
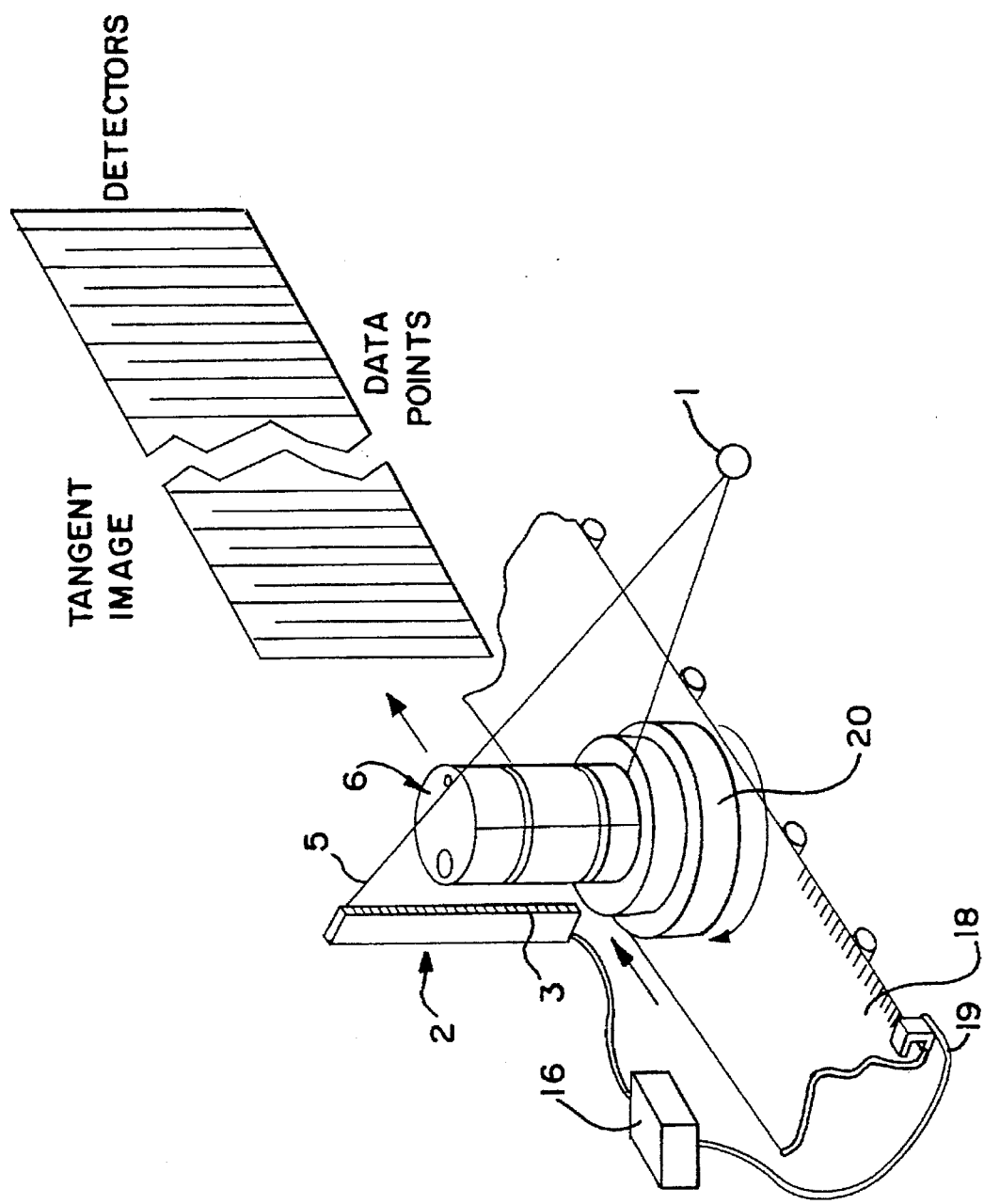
FIG. 6 is a perspective of a tangential CT scanner having an object translated along a linear path.

Alternatively, FIG. 6 shows an embodiment where the drive device consists of a conveyor system 18 and a turntable 20 mounted on the conveyor system 18. The object 6 is supported by the turntable 20, which rotates the object 6 within the energy fan-beam 5. The rotating object 6 is then translated through the fan-beam 5 by the conveyor system 18. With such an embodiment, the conveyor system 18 is marked with positioning markings for detection by encoders that read the markings. The encoder allows the computer to record the exact position for each reading. Similarly, the rotational device, or turntable 20, has markings which can be recorded by the computer for each data point reading.

The encoder on the rotational turntable 20 marks the exact azimuthal location of the object 6. Again, these encoder readings are useful for locating the flaw in the object and for back projection of cross-sectional CT slice image reconstruction.

Figure 4:
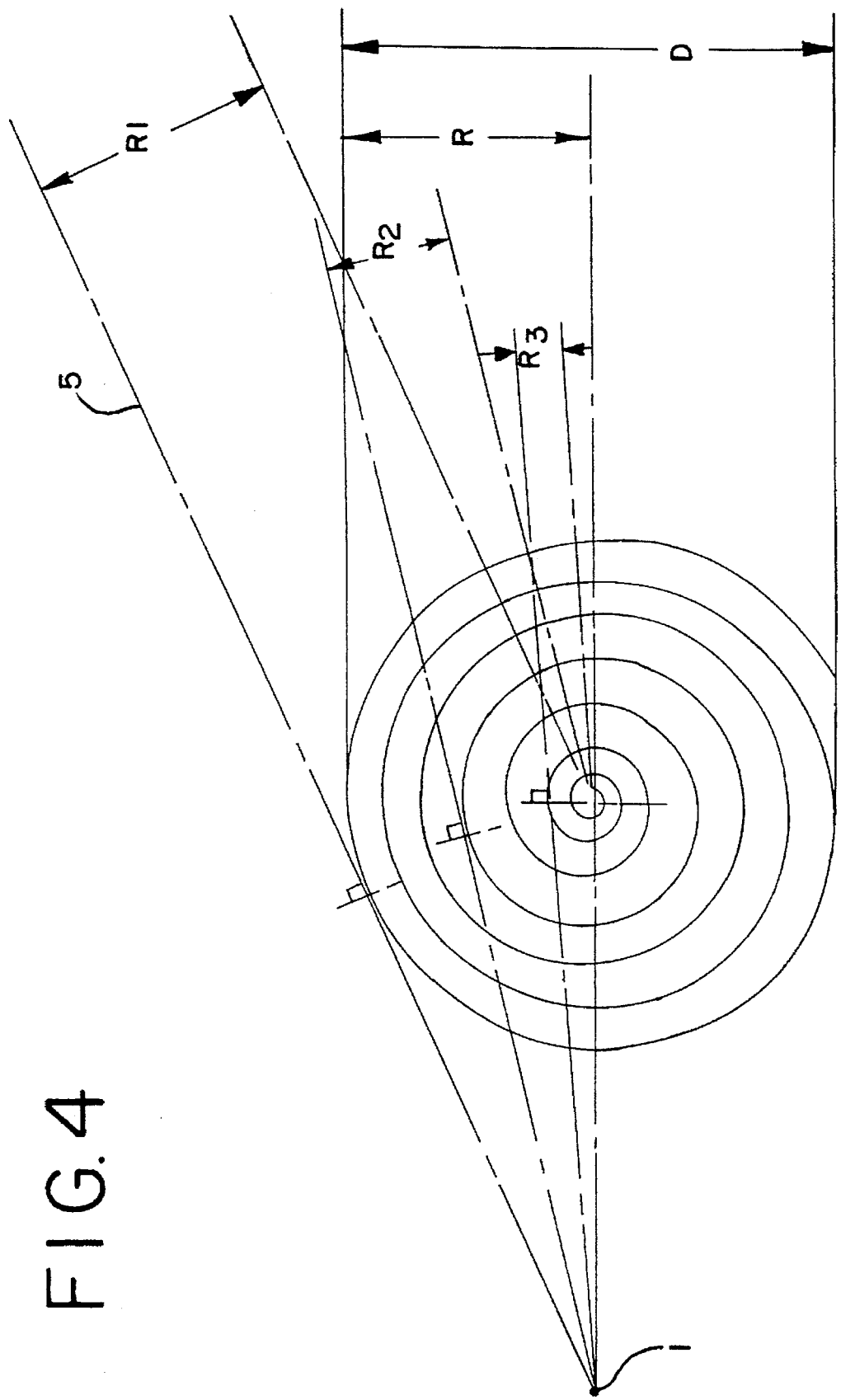
FIG. 4 is a tangential path cut by a radiation fan beam having an arcuate path about an object.

When using the gantry embodiment as shown in FIGS. 1 and 2, the fan-beam 5 is translated past the rotating object 6 by moving the detector array 2 relative to the spinning object 6 as shown in FIGS. 1 and 4. Typically, the rate of translation is in the range of about 1 inch/minute to 10 inches/minute. The location of the object 6 is noted for each data point reading by recording the exact position of the array 2 as it rotates about the object 6. Alternatively, the object can be translated in a direction perpendicular to the plane defined by the beam of penetrating energy. Translation can be either linear or arcuate. In either case, the position of the object 6 relative to the beam 5 is recorded for each data point reading.

An example of arcuate translation is shown in FIGS. 1 and 4, where the detector array 2 is slowly rotated about a focal point 13 containing the energy source 1. An arm 12, depicted as a C-shaped arm, is attached at one end to a frame 17 at the focal point 13. The detector array 2 is connected to the other end of the arm 12. An actuator 14 is attached to a midpoint of the arm 12 and to a first support bracket 50 at pivot point 15. The first support bracket 50 is mounted on the frame 17. A support arm 40 also interconnects the arm 12 and a second support bracket 52 mounted on the frame 17. As the actuator 14 extends or retracts, it rotates about the pivot point 15 and causes the arm 12 to rotate about the focal point 13. Thus, the fan-beam 5 is translated through the object 6. Translation of the fan-beam 5 is in a direction perpendicular to the plane of the fan-beam 5 as shown in FIG. 4.

As it rotates, the fan-beam 5, formed between the energy source 1 and the detectors 3, forms a tangential path in the object 6. As the object 6 is translated through the beam 5, the diameter of the tangential path is varied. The detectors 3 measure the energy intensity through all possible tangents of the object 6 as the fan-beam 5 is moved across the diameter of the object 6. For example, in FIG. 4, the fan-beam 5 is shown tangentially passing through the object 6 at radii R1, R2 and R3. Because the object 6 simultaneously rotates and translates through the fan-beam 5, data defining the object 6 is collected in a spiral form. By analogy, the object 6 resembles a roll of paper towels being unrolled a single layer at a time. Data is typically collected at a rate of about 100,000 to 500,000 readings/second.

For a typical 180 degree scan, the translation involves placing the fan-beam 5 at a tangent to the object's outermost diameter and passing the fan-beam 5 through the object 6 to the center of the object 6 or until the entire radius (R) of the object 6 is covered by the tangential path as shown in FIG. 4. A 360 degree scan requires scanning from the outer diameter of the object 6 to the other outer diameter, or until the full diameter (D) of the object 6 is covered by the tangential path. Alternatively, the object 6 can be scanned from a predetermined diameter to another predetermined diameter. With this invention, therefore, the collection of extraneous data is avoided with all types of scans, including the 180 degree and the 360 degree scan. In contrast, third and fourth generation scanner systems collect useless data when the diameter of the object is less than the size of the x-ray fan-beam. Because the tangential CT scanner's beam 5 is started at the object's outer diameter, and stopped when it reaches either the center, the opposite end of the diameter or any other predetermined diameter, no extraneous data is generated or collected.

As the fan-beam 5 traverses the rotating object 6, each detector 3 collects data for one cross-sectional slice of the object 6. A cross-section slice is defined as that area being scanned by one detector 3 and is typically an area lying perpendicular to the axis of rotation 8 and the plane of the beam 5. Therefore, the data collected for each cross-section is collected by a single detector 3. Because only one detector 3 is utilized for each cross-sectional slice, the tangential scanner does not produce any artifacts due to detector variations. Furthermore, as the fan-beam 5 passes over the object 6, all detectors 3 in the detector array 2 simultaneously collect data for a different cross-sectional slices at their respective levels. Therefore, data is collected for the entire volume of the object 6 with only one translational pass. This data can be reconstructed later by computer software into a variety of images representing the interior of the object.

To obtain better resolution of the images generated from the collected data, the rotation and translation speeds can be varied to increase the number of rays collected. Rays are defined as the number of data points collected across the diameter of the object 6. The views represent the number of directions from which the data points are collected through the object 6. The number of rays and views determine the ultimate resolution of the reconstructed cross-sectional image. In the tangential scanner system, the number of rays in the data set is equal to the number of rotations experienced during the data collection. Accordingly, as the number of rays, i.e. rotations, is increased, better spatial resolution is achieved. Conversely, the number of rotations can be limited to reduce overall scanning time.

Resolution is also dictated by the number of data points or views collected during any single rotation. The more points collected, the better the spatial resolution. Again, the rotation and translation speeds can be altered to permit more or less data point readings. In essence, the tangential system can collect data with any number of rays and views simply by varying the rotation and translation speed parameters, or data collection rate. There is no limitation, therefore, to the number of rays or views in the collected data sets that are used to reconstruct the object displays or images.

A system computer 23 is used to collect the data from each detector 3 in the array 2. The computer 23 responds to the resulting signals from the detectors 3 to construct a tomographic x-ray image of the object 6. The computer system 23 communicates with the detector array 3 through communication links 30.

Figure 5:
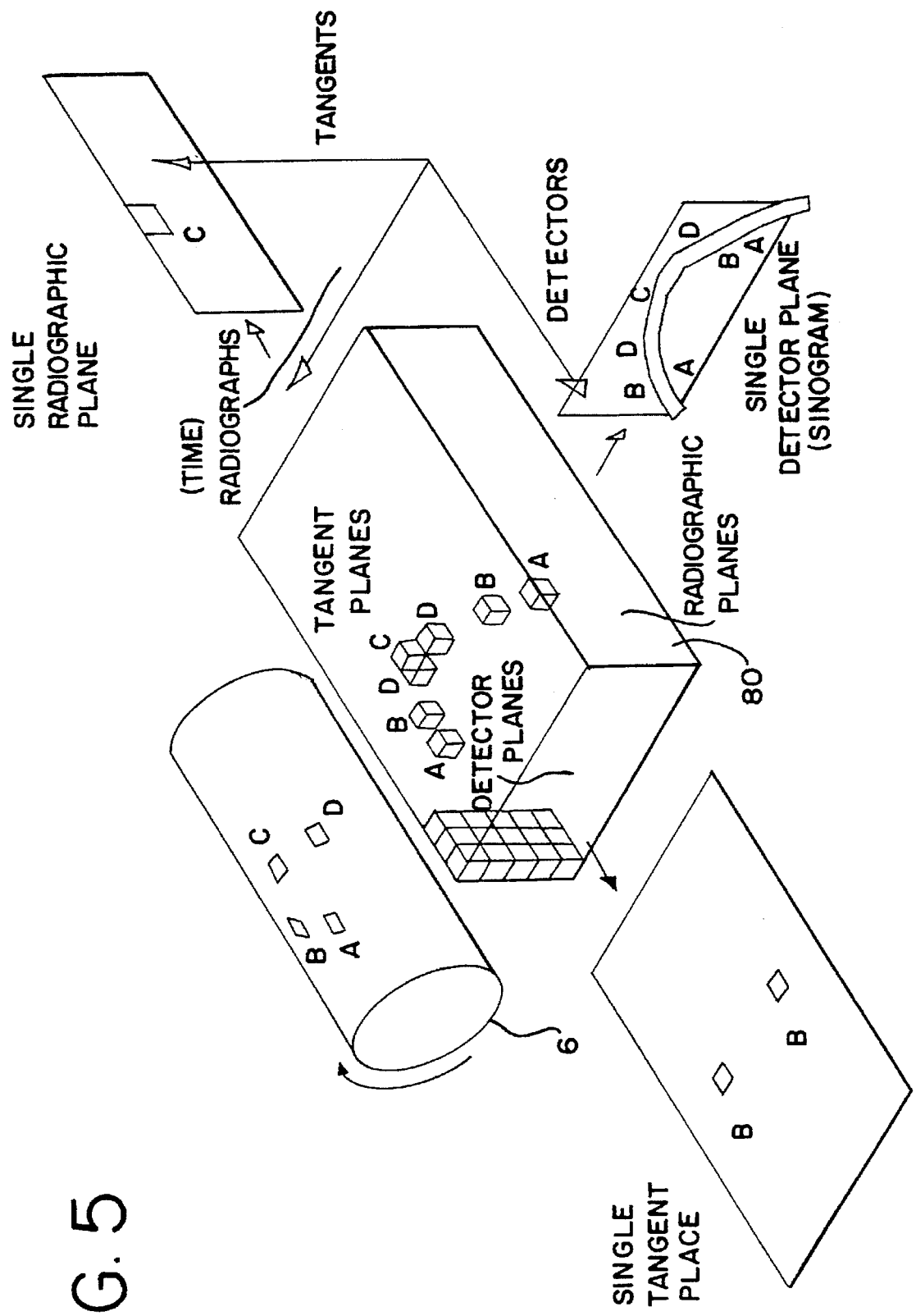
FIG. 5 is a pictorial of a data volume set generated by a tangential CT scanner.

For a meaningful display of the tangential data set, the entire data set is organized in the computer system's memory. In an exemplary method for data collection, the tangential data is organized for each successive layer in the object 6. First, a two dimensional plane of data is generated. The number of detectors 3 in the detector array 2 represent one axis of this data plane and the number of data points taken through one 360 degree rotation represents the other axis of the plane, as shown in FIGS. 5 and 6. Many such data planes are generated, where each data plane represents one rotation of the object 6. These data planes are then stacked one over the other for successive rotations (layers) of the object 6 to organize a cube of data, or data cube 80, in the computer memory as shown in FIG. 5.

A layer of data is made up of a tangential data sets collected at successively different depth levels in the object 6. Data collected and stored in this manner can be utilized in a variety of ways for visually displaying computer generated images for data analysis. Typically, a processor 16 equipped with software or logic, reconstructs the data into three types of images on a computer screen 65, or display unit such as a CRT. The three modes of display correspond to viewing the image of the data cube 80 through three perpendicular planes. In the first mode, the system displays the tangential planes, as they were stacked originally.

In the second mode, various vertical cuts through the data cube are displayed. This mode shows the entire data collected by a single detector 3. The data in this mode is similar to the sinogram data from any conventional CT scanner system. This data can be used to reconstruct the cross-sectional image of CT slices. The data from each detector 3 represents one CT slice.

In the third mode, various horizontal cuts through the data cube 80 are displayed. This mode show the entire data set collected through a single orientation of the object 6 and it is equivalent to a radiographic view of the object 6. Many such radiographic views are available through various orientations of the object.

The first mode, or the tangent display, is equivalent to unrolling a roll of paper one layer at a time. Each unrolled sheet can be individually displayed. Data displayed in this mode is very sensitive to defects located parallel to the surface of the object 6 such as unbond defects in rocket motor casings. Within a single layer of the tangent data, features of the object 6, such as unbond defects, will show up once in the data when the x-ray beam 5 is exactly at the tangent of the defect. The same feature shows up twice in the display when the x-ray beam is inside the "object" circle, i.e., once when the defect is towards the x-ray tube and again when it is towards the detector side.

In the second mode, the data is displayed in the form of sinograms. In this mode, the computer 23 displays the data for an individual slice of each cross-section of the object 6. Each sinogram display is created from data points gathered by a single detector 3. The individual sinogram from each detector 3 is a complete set of raw data which can be used to reconstruct individual CT slices. Therefore, the number of possible sinogram displays is directly correlated to the number of detectors 3. Because each sinogram display is organized from data gathered by one detector 3, the sinogram display does not contain any artifacts. A sinogram has an amplitude and a phase corresponding, respectively, to the radial and azimuthal locations of the feature being displayed. The intensity of the sinogram curve demonstrates the size of the feature being analyzed.

The third and final mode for displaying the data is the radiographic display. Such a display shows the data collected in a plane cutting the data cube 80 along a fixed azimuthal angle, or the data corresponding to the image of the object without rotation. Successive similar cross sections show digital radiographs of the object 6 as it rotates around its axis. The radiographic display is helpful in extracting the location and intensity of the features. Together, all three display modes provide a better understanding of the feature being evaluated.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

I claim:

1. A tangential computed tomography scanner for scanning an object having an axis and at least one cross-section perpendicular to said axis, said scanner comprising:
    an energy source adapted to emit penetrating energy;
    a detector array having a plurality of detectors positioned in an elongated array, said detector array adapted to receive a planar beam of said penetrating energy from said source, said array oriented such that said planar beam lies generally parallel to said axis of said object and generally perpendicular to said cross-section of said object;
    a drive device adapted to translate one of said beam and said object relative to the other of said beam and said object along a path substantially perpendicular to the plane of said beam, and also adapted to rotate said object about said axis concurrently with said translation.

2. A tangential computed tomography scanner according to claim 1 wherein said drive device is adapted to translate said beam relative to said object along said path.

3. The scanner according to claim 2 wherein said drive device comprises an arm connected at one end to a focal point, said detector array connected to said arm opposite said focal point, and an actuator attached to said arm, said actuator adapted to rotate said arm and said detector array about said focal point.

4. The scanner according to claim 3 wherein said drive device further comprises at least a pair of rollers supporting said object, wherein one of said rollers is adapted to induce rotation of said object.

5. A tangential computed tomography scanner according to claim 1 wherein said drive device is adapted to translate said object along said path such that said object is interposed in said beam between said source and said array.

6. The scanner according to claim 2 or 5 wherein said path is linear.

7. The scanner according to claim 2 or 5 wherein said path is arcuate.

8. The scanner according to claim 5 wherein said drive device comprises a conveyor system and a turntable mounted on said conveyor system, whereby said object can be rotated about said axis of rotation concurrently with said translation.

9. The scanner according to claim 7 wherein said source of penetrating energy is positioned at the center of said arcuate path.

10. The scanner according to claim 3 wherein said source of penetrating energy is positioned at the focal point.

11. The scanner according to claim 1 further comprising a memory adapted to store data collected from said detector array, wherein a layer of data is collected for each detector in said array, said layers of data positioned in a data cube within said memory.

12. The scanner according to claim 11 further comprising a processor responsive to said collected data including logic adapted to construct and display the data in a sinogram display.

13. The scanner according to claim 11 further comprising a processor responsive to said collected data including logic adapted to construct and display said data in a radiographic display.

14. The scanner according to claim 11 further comprising a processor responsive to said collected data including logic adapted to construct and display said data in a tangent display.

15. The scanner according to claim 1 wherein said penetrating energy source is an x-ray.

16. The scanner according to claim 1 wherein said axis of rotation is an axis of symmetry.

17. The scanner according to claim 1 wherein said axis of rotation is asymmetrical.

18. The scanner according to claim 1 wherein said object is a rocket motor.

19. The scanner according to claim 1 wherein said object is a drum.

20. A method for scanning an object with a tangential computed tomography scanner, said object having an axis and at least one cross-section perpendicular to said axis, said method comprising:

emitting penetrating energy from a source;

receiving a planar beam of said penetrating energy with a plurality of detectors positioned in an elongated array, said array oriented such that said planar beam lies generally parallel to said axis and generally perpendicular to said cross-section of said object;

translating one of said beam and said object relative to the other of said beam and said object along a path substantially perpendicular to the plane of said beam;

rotating said object about said axis concurrently with said translation; and reading data points from each detector as one of said beam and said object moves relative to the other of said beam and said object.

21. The method of claim 20 wherein said step of translating comprises:

translating said beam along said path so as to interpose said object in said beam between said source and said array.

22. The method of claim 20 wherein said step of translating further comprises:

scanning said object from a first predetermined radius to the center of the object.

23. The method of claim 20 wherein said step of translating further comprises:

scanning said object from a first predetermined radius to a second predetermined radius.

24. The method of claim 20 wherein said step of translating said beam further comprises:

scanning across the entire diameter of said object.

25. The method of claim 20 further comprising:

scanning said object; and storing said data points in a computer memory.

26. The method of claim 25 further comprising:

constructing a tomographic image of said object on a display with a processor.

27. The method of claim 26 wherein said step of constructing a tomographic image further comprises constructing a radiographic image.

28. The method of claim 26 wherein said step of constructing a tomographic image further comprises constructing a sinogram display.

29. The method of claim 26 wherein said step of constructing a tomographic image further comprises constructing a tangent display.

30. The method of claim 20 wherein said step of translating comprises:

translating said object along a path substantially perpendicular to said beam.

31. A tangential computed tomography scanner for scanning an object having an axis, said scanner comprising:

an energy source adapted to emit penetrating energy;

a detector array having a plurality of detectors positioned in an elongated array, said detector array adapted to receive a planar beam of said penetrating energy from said source, said array oriented such that said planar beam lies generally parallel to said axis of said object, said object disposed in said beam;

a drive device adapted to rotate said object about said axis.

* * * * *